(12) United States Patent
Boden et al.

(10) Patent No.: US 7,700,721 B2
(45) Date of Patent: Apr. 20, 2010

(54) BETA SHEET TAPES RIBBONS IN TISSUE ENGINEERING

(75) Inventors: Neville Boden, Leeds (GB); Amalia Agelli, Leeds (GB); Eileen Ingham, Leeds (GB); Jennifer Kirkham, Leeds (GB)

(73) Assignee: University of Leeds, Leeds (GB)

( * ) Notice: Subject to any disclaimer, the term of this patent is extended or adjusted under 35 U.S.C. 154(b) by 27 days.

(21) Appl. No.: 10/521,628

(22) PCT Filed: Jul. 15, 2003

(86) PCT No.: PCT/GB03/03016

§ 371 (c)(1),
(2), (4) Date: Sep. 8, 2005

(87) PCT Pub. No.: WO2004/007532

PCT Pub. Date: Jan. 22, 2004

(65) Prior Publication Data

US 2006/0154852 A1    Jul. 13, 2006

(30) Foreign Application Priority Data

Jul. 15, 2002    (GB) ................................ 0216286.5

(51) Int. Cl.
- *A61K 38/04* (2006.01)
- *A61K 38/08* (2006.01)
- *A61K 38/10* (2006.01)
- *A61K 9/00* (2006.01)
- *A61K 9/70* (2006.01)
- *C07K 4/00* (2006.01)
- *C07K 7/00* (2006.01)
- *C07K 14/00* (2006.01)

(52) U.S. Cl. ................... 530/327; 530/300; 530/324; 530/325; 530/326; 514/2; 514/12; 514/13; 514/14; 514/15

(58) Field of Classification Search .......... None
See application file for complete search history.

(56) References Cited

U.S. PATENT DOCUMENTS

| 6,034,211 A | 3/2000 | Kelly |
| 2003/0162696 A1* | 8/2003 | Mihara .......................... 514/8 |

FOREIGN PATENT DOCUMENTS

WO    WO 03/006494 A1    1/2003

OTHER PUBLICATIONS

Aggeli A, Fytas G, Vlassopoulos D, McLeish TCB, Mawer PJ, Boden N, Structure and Dynamic of Self-Assembing beta-sheet Peptide Tapes by Dynamic Light Scattering, Biomacromolecules, 2001, 2: 378-388.*
Aggeli A, Bell M, Strong A, Radford S and Boden N, Self-assembling homopolymeric peptide tapes in aqueous solution, Peptide Science-Present and FUture, 1999, 30-33.*
Aggeli et al., "Responsive Gels Formed by the Spontaneous Self-Assembly of Peptides Into Polymeric β-Sheet Tapes," *Nature* 386:259-262 (1997).
Aggeli et al, "pH as a Trigger of Peptide β-Sheet Self-Assembly and Reversible Switching between Nematic and Isotropic Phases," *J. Am. Chem. Soc.* 125:9619-9628 (2003).
Fishwick et al., "Structures of Helicalf β-Tapes and Twisted Ribbons: The Role of Side-Chain Interactions on Twist and Bend Behavior," *Nano Lett.* 3:1475-1479 (2003).
Fukushima, "Self-Induced Helix-Sheet Conformational Transitions of an Amphiphilic Peptide," *Polym. J.* 27:819-830 (1995).
Nyrkova et al., "Fibril Stability in Solutions of Twisted β-Sheet Peptides: A New Kind of Micellization in Chiral Systems," *Eur. Phys. J.* 17:481-497 (2000).
Nyrkova et al., "Self-Assembly and Structure Transformations in Living Polymers Forming Fibrils," *Eur. Phys. J.* 17:499-513 (2000).

* cited by examiner

*Primary Examiner*—Anish Gupta
*Assistant Examiner*—Julie Ha
(74) *Attorney, Agent, or Firm*—Klarquist Sparkman, LLP

(57) ABSTRACT

There is described a material comprising ribbons, fibrils or fibres characterised in that each of the ribbons, fibrils or fibres have an antiparallel arrangement of peptides in a beta-sheet-tape-like substructure.

48 Claims, 8 Drawing Sheets

Peptides designed to form heteropolymeric tapes in water

Peptides can be designed to have complementary electric charges, such that, when mixed, tape self-assembly and subsequent gel formation occur spontaneously.

An anti-parallel β-sheet dimer of DN1-ORN2Q and DN1-2E peptides

A = DN1-ORN2Q
B = DN1-2E

| COMPONENTS | Mole, Weight | Concentration (mg/L) | Molarity (mM) |
|---|---|---|---|
| INORGANIC SALTS: | | | |
| Calcium Nitrate-4H2O | 236 | 100.00 | 0.424 |
| Potassium Chloride | 75 | 400.00 | 5.30 |
| Magnesium Sulphate-7H2O | 246 | 100.00 | 0.407 |
| Sodium Chloride | 58 | 6000.00 | 103.00 |
| Sodium Bicarbonate | 84 | 2000.00 | 23.800 |
| Sodium Phosphate Dibasic-7H2O | 268 | 1512.00 | 5.63 |
| OTHER COMPONENTS: | | | |
| Glucose | 180 | 2000.00 | 11.10 |
| Glutathione Reduced | 307 | 1.00 | 0.0032 |
| Phenol red | 398 | 5.00 | 0.0125 |
| AMINO ACIDS: | | | |
| L-Arginine | 174 | 200.00 | 1.10 |
| L-Asparagine | 132 | 50.00 | 0.379 |
| L-Aspartic Acid | 133 | 20.00 | 0.150 |
| L-Cystine 2HCl | 313 | 65.00 | 0.208 |
| L-Glutamic Acid | 147 | 20.00 | 0.136 |
| Glycine | 75 | 10.00 | 0.133 |
| L-Histidine | 155 | 15.00 | 0.0967 |
| L-Hydroxyproline | 131 | 20.00 | 0.153 |
| L-Isoleucine | 131 | 50.00 | 0.382 |
| L-Leucine | 131 | 50.00 | 0.382 |
| L-Lysine HCl | 146 | 40.00 | 0.219 |
| L-Methionine | 149 | 15.00 | 0.101 |
| L-Phenylalanine | 165 | 15.00 | 0.0909 |
| L-Proline | 115 | 20.00 | 0.174 |
| L-Serine | 105 | 30.00 | 0.286 |
| L-Threonine | 119 | 20.00 | 0.186 |
| L-Tryptophan | 204 | 5.00 | 0.0245 |
| L-Tyrosine 2Na | 225 | 29.00 | 0.110 |
| L-Valine | 117 | 20.00 | 0.171 |
| VITAMINS: | | | |
| Biotin | 244 | 0.2 | 0.008 |
| D-Ca Pantothenate | 477 | 0.25 | 0.0005 |
| Choline Chloride | 140 | 3.00 | 0.0214 |
| Folic Acid | 441 | 1.00 | 0.0022 |
| i-Inositol | 180 | 35.00 | 0.194 |
| Niacinamide | 122 | 1.00 | 0.0081 |
| p-Aminobenzoic Acid (PABA) | 137 | 1.00 | 0.0072 |
| Pyridoxine HCl | 206 | 1.00 | 0.0048 |
| Riboflavin | 376 | 0.20 | 0.0005 |
| Thiamine HCl | 337 | 1.00 | 0.0029 |
| Vitamin B12 | 1355 | 0.005 | 0.00000369 |

Fig. 5/Table 2

SEQUENCE LISTING

<160> NUMBER OF SEQ ID NOS: 7

<210> SEQ ID NO 1
<211> LENGTH: 11
<212> TYPE: PRT
<213> ORGANISM: Artificial
<220> FEATURE:
<223> OTHER INFORMATION: Synthetic peptide

<400> SEQUENCE: 1

Gln Gln Arg Gln Gln Gln Gln Gln Glu Gln Gln
1               5                   10

<210> SEQ ID NO 2
<211> LENGTH: 11
<212> TYPE: PRT
<213> ORGANISM: Artificial
<220> FEATURE:
<223> OTHER INFORMATION: Synthetic peptide

<400> SEQUENCE: 2

Gln Gln Arg Phe Gln Trp Gln Phe Glu Gln Gln
1               5                   10

<210> SEQ ID NO 3
<211> LENGTH: 11
<212> TYPE: PRT
<213> ORGANISM: Artificial
<220> FEATURE:
<223> OTHER INFORMATION: Synthetic peptide

<400> SEQUENCE: 3

Gln Gln Arg Phe Glu Trp Glu Phe Glu Gln Gln
1               5                   10

<210> SEQ ID NO 4
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa represents ornithine
<220> FEATURE:
<221> NAME/KEY: MISC_FEATURE
<222> LOCATION: (5)..(5)
<223> OTHER INFORMATION: Xaa represents ornithine
<220> FEATURE:
<221> NAME/KEY: MISC_FEATURE
<222> LOCATION: (7)..(7)
<223> OTHER INFORMATION: Xaa represents ornithine

<400> SEQUENCE: 4

Gln Gln Xaa Phe Xaa Trp Xaa Phe Gln Gln Gln
1               5                   10

<210> SEQ ID NO 5
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa represents ornithine

```
<220> FEATURE:
<221> NAME/KEY: MISC_FEATURE
<222> LOCATION: (7)..(7)
<223> OTHER INFORMATION: Xaa represents ornithine

<400> SEQUENCE: 5

Gln Gln Arg Phe Xaa Trp Xaa Phe Glu Gln Gln
1               5                   10

<210> SEQ ID NO 6
<211> LENGTH: 11
<212> TYPE: PRT
<213> ORGANISM: Artificial
<220> FEATURE:
<223> OTHER INFORMATION: Synthetic peptide

<400> SEQUENCE: 6

Gln Gln Glu Phe Glu Trp Glu Phe Glu Gln Gln
1               5                   10

<210> SEQ ID NO 7
<211> LENGTH: 10
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa represents ornithine
<220> FEATURE:
<221> NAME/KEY: MISC_FEATURE
<222> LOCATION: (5)..(5)
<223> OTHER INFORMATION: Xaa represents ornithine
<220> FEATURE:
<221> NAME/KEY: MISC_FEATURE
<222> LOCATION: (7)..(7)
<223> OTHER INFORMATION: Xaa represents ornithine
<220> FEATURE:
<221> NAME/KEY: MISC_FEATURE
<222> LOCATION: (9)..(9)
<223> OTHER INFORMATION: Xaa represents ornithine

<400> SEQUENCE: 7

Gln Gln Xaa Phe Xaa Trp Xaa Phe Xaa Gln
1               5                   10
```

BETA SHEET TAPES RIBBONS IN TISSUE ENGINEERING

This is the U.S. National Stage of International Application No. PCT/GB2003/003016, filed Jul. 15, 2003 (published in English under PCT Article 21 (2)), which in turn claims the benefit of Great Britain patent application no. 0216286.5 filed Jul. 15, 2002.

BACKGROUND

This invention relates to novel supramolecular aggregates, polymers and networks made by beta-sheet self-assembly of rationally-designed peptides, and their uses as for example as responsive industrial fluids (oil exploration), as personal care products, as tissue reconstruction devices, or as controlled drug delivery systems.

International Patent Application No WO 96/31528, Boden, et al describes novel rationally designed peptides which self-assemble in one dimension to form beta sheet tape-like polymers. The tapes above a critical peptide concentration (typically above 0.3% v/v peptide) become physically entangled and gel their solutions in organic solvents or in water (FIG. 1). The peptide gels possess the specific property of being programmable to switch from the gel state to a fluid or stiffer gel state in response to external chemical or physical triggers.

DETAILED DESCRIPTION

It has recently been found that the tapes having chemically distinct opposing surfaces can give rise to an hierarchy of other self-assembled, supramolecular structures as a function of increasing peptide concentration: ribbons (two stacked tapes), fibrils (many ribbons stacked together) and fibres (entwined fibrils) [1-3] (FIG. 2). All these beta-sheet polymers appear twisted because of the peptide chirality. A theoretical model has been developed which rationalises this self-assembly process of beta-sheet forming peptides using a set of energetic parameters $\epsilon_j$ (FIG. 1). The magnitudes of $\epsilon_j$ define the peptide concentration ranges over which each type of polymer will be stable.

We have shown that by appropriate peptide design we can produce tapes, ribbons, fibrils or fibres controllable by changes of the pH, the ionic strength of the solution or temperature. In particular, peptides can be designed which self-assemble to form one or other of these polymers at a certain concentration and in a specific pH range, but which are transformed into another polymer structure or dissociate into the monomeric random coil state in a different pH range, according to the specification of the amino acid sequence of the peptide.

We have recently discovered that this hierarchy of polymers can be formed not only by a single type of peptide (homopeptide polymers), but most importantly also by mixing complementary peptides together (alternating co-polymers). For example, we have shown that peptide P11-3 (also known as DN1-2E: SEQ ID NO: 3) (Table 1) adopts monomeric random coil conformation and forms fluid isotropic solutions at pH>7 in water. This behaviour stems from the three glutamate groups on the peptide. At pH higher than their effective pKa, the glutamate side-chains are ionised, and the intermolecular electrostatic repulsions generated by these negatively charged groups prevent beta-sheet self-assembly. Similarly peptide P11-4 (SEQ ID NO: 4) adopts monomeric random coil conformation and forms fluid solutions at pH<7.5 in water. This behaviour stems from the electrostatic repulsions generated between the positively charged ornithine groups (four ornithines per peptide). However, when a solution of P11-3 (SEQ NO: 3 negatively charged) is mixed with a solution of P11-4 (SEQ ID NO: 4: positively charged) above a certain critical peptide concentration (typically in the micromolar region), there is instant beta-sheet self-assembly into ribbons, fibrils, or fibres, according to the peptide concentration, and these are formed by an alternating arrangement of the complementary peptides: P11-3 (SEQ ID NO: 3) and P11-4 (SEQ ID NO: 4) etc (FIG. 3).

Thus, according to the invention we provide a material comprising ribbons, fibrils or fibres characterised in that each of the ribbons, fibrils or fibres have an antiparallel arrangement of peptides in a β-sheet tape-like substructure.

When the material substantially comprises fibrils, the fibrils may be comprised in a network of fibrils interconnected at fibre-like junctions.

We also provide a material wherein the material comprises a self assembling peptide (SAP) wherein the SAP forms a tape in an aqueous medium and is made up of 3 or more polar/neutral amino acids and a plurality of charged amino acids.

The polar/neutral amino acids, which may be the same or different, and are selected from the group including glutamine, serine, asparagine, orthinine, cysteine, lycine, histidine, glutamic acid and threonine.

We further provide a material wherein the amino acids are positively charged and form a gel at a pH of less than or equal to a neutral pH. Alternatively, we provide a material wherein the amino acids are negatively charged and form a gel at a pH of greater than or equal to a neutral pH.

A material in this aspect of the invention is SAP is P11-1 (SEQ ID NO: 1).

We further provide a material wherein the amino acid chain is extended to include a bioactive peptide sequence, or wherein the amino acid chain is attached to a therapeutically active molecule.

The material may comprise an SAP which forms ribbons and/or fibrils in an aqueous solution and wherein the SAP has a primary structure in which at least 50% of the amino acids comprise an alternating structure of polar and apolar amino acids.

The polar amino acids include from 1 to 3 charged amino acids per 11 amino acids. Preferably, the SAP is selected from the group P11-2 (SEQ ID NO: 2), P11-3 (SEQ ID NO: 3), P11-4 (SEQ ID NO: 4) and P11-5 (SEQ ID NO: 5; also known as DN1-2O).

The material may be suitable for use in, inter alia, tissue engineering, cell culture medium, and/or dental treatment.

We also provide a material wherein the material comprises a self assembling peptide (SAP) wherein the SAP forms a tape in an aqueous medium and is made up of 3 or more polar/neutral amino acids and a plurality of charged amino acids.

The polar/neutral amino acids, which may be the same or different, may be selected from the group including glutamine, serine, asparagine, orthinine, cysteine, lycine, histidine, glutamic acid and threonine.

The apolar amino acids, which may be the same or different, and are selected from the group including phenylalanine, tryptophan, valine, leucine, isoleucine and methionine.

We further provide a material wherein the amino acid chain is extended to include a bioactive peptide sequence, or wherein the amino acid chain is attached to a therapeutically active molecule.

Preferably, in this aspect of the invention the SAP is P11-3 (SEQ ID NO: 3).

We also provide a material wherein the SAP is soluble in a highly ionic medium. In this aspect of the invention, the SAP may comprise a ratio of net charged amino acids to total amino acids of from 1:1 to 4:11.

The material may be suitable for use in, inter alia, tissue engineering, cell culture medium, and/or dental treatment.

We further provide a material wherein the complementary peptide tapes are made up of 3 or more polar amino acids of which some are charged amino acids wherein the ratio of charged amino acids to total amino acids is 3:11 or greater.

Thus, the SAP may be selected from the group P11-6 (SEQ ID NO: 6) and P10-7 (SEQ ID NO: 7).

We further provide a material wherein the amino acid chain is extended to include a bioactive peptide sequence, or wherein the amino acid chain is attached to a therapeutically active molecule.

The material may be suitable for use in, inter alia, tissue engineering, cell culture medium, and/or dental treatment.

Thus, according to a further feature of the invention we provide alternate co-polymer beta-sheet polymeric tapes, ribbons, fibrils and fibres made by the self-assembly of more than one complementary peptides. The complementarity of the peptide may be originating from their charges e.g. net positive charge on one peptide and net negative charge on the other peptide.

The tapes, ribbons, fibrils and fibres are increasingly more rigid structures [1]. For example we have found that the persistence length l of single tapes formed by an 11-residue peptide P11-1 (SEQ ID NO: 1) in water is ca 0.3 μm, whilst the persistence lengths of ribbons and fibrils formed by a variant P11-2 peptide (SEQ ID NO: 2) in water are 1 and 20-70 μm respectively (Table 1).

We have also shown that above a certain peptide concentration $c_{I/N}$ (isotropic to nematic transition concentration) the semi-rigid ribbons, fibrils and fibres can align and thus transform their initially isotropic solution into a nematic liquid crystalline solution. The transition of the solution to the nematic liquid crystalline state happens at lower concentrations for more rigid polymers. For example, the nematic transition for solutions of ribbons of P11-1 (SEQ ID NO: 1) peptide occurs at $c_{I/N} \approx 13$ mM, whilst the nematic transition for solutions of the much more rigid fibrils of P11-2 peptide (SEQ ID NO: 2) occurs at $c_{I/N} \approx 0.9$ mM.

We have also shown that as the peptide concentration increases even further there is a second transition from a fluid nematic liquid crystalline solution to a self-supporting nematic gel, which is formed by the entwining of the fibrils (FIG. 4).

We have discovered that the alignment of these polymers (tapes, ribbons, fibrils and fibres) can be improved significantly by shearing or application of external magnetic field to the peptide solution. Subsequent gelation locks the aligned polymers into place and preserves their alignment for a long time (typically weeks) even after the polymer solution is removed from the magnetic field or after the end of shearing. Shearing or external magnetic field (superconducting magnet with a field strength of 7T) have been found indeed to improve the alignment of fibrils in aqueous solutions of P11-2 peptide (SEQ ID NO: 2), as shown by monitoring the birefringence of the solution using cross polars. The improved polymer alignment in solution has been preserved for several weeks after the end of shearing or of the application of the magnetic field.

Thus according to the invention we provide a method of producing nematic liquid crystalline solutions and gels of homopeptide or alternating copeptide beta-sheet tapes, ribbons, fibrils or fibres with improved polymer alignment and thus improved optical properties (i.e. increased liquid crystallinity and birefringence), by shearing the peptide solutions or by subjecting them to other external forces such as electric and magnetic fields.

These peptide liquid crystalline solutions and gels can be formed in organic solvents or in water depending on the peptide design. The design of the peptide primary structure is necessary to achieve compatibility between the surface properties of the peptide polymers and the solvent. For example, self-assembling beta-sheet forming peptides with predominantly hydrophobic amino acid side-chains are required to form nematic solutions and gels in moderately polar solvents, whilst peptides which form tapes with at least one polar side are required to obtain nematic solutions and gels in water.

The fibrils and fibres are alignable and can therefore form nematic gels. Therefore, the fibrils and fibres can be spun to make, for example, high tensile strength fibres, cf. Kevlar®. Also, they can be used to make highly ordered scaffolds for tissue engineering or templates for the growth of inorganic matrices, or as matrices for the alignment of biomolecules, e.g. in NMR spectroscopy.

Until recently, formation of these polymers has been limited to relatively simple solutions (e.g. pure solvents or low ionic strength solutions). We have now discovered that it is possible to rationally design peptides which will form soluble polymers (i.e. tape, ribbons, fibrils and fibres) in more complex biologically relevant fluids, for example in cell media. These are complex mixtures used for growing and maintaining cells, because they mimic the natural environment of the cell in vivo (for the composition of typical cell media see FIG. 5). The issue of polymer solubility in these media is of practical importance. The reason is that biological fluids and cell media are characterised by relatively high ionic strength, equal to about 145 mM NaCl, which tends to cause polymers to precipitate. We have discovered that in order to produce soluble peptide polymers in these solutions, it is necessary to build an appropriate degree of repulsion between the polymers to keep them apart in solution. Stable three-dimensional gel scaffolds can be produced in cell media in this way, which precipitate from solution.

The stages of peptide design for formation of soluble beta-sheet polymers and gel scaffolds in cell media are:
1) for production of single tapes, design the peptide following the criteria in the International Patent Application No. PCT/GB96/00743. To produce stable single tapes in cell media, both sides of tapes should be covered by predominantly polar groups.
2) for production of ribbons, fibrils and fibres, one sides of the tape should be different from the other, e.g. one predominantly polar and the other predominantly apolar. The polar sides should also be able to weakly interact with each other e.g. through hydrogen-bonding sites provided for example by glutamine or asparagines side chains.
3) To ensure all these polymers are soluble in cell media, some repulsion between polymers must be created. This can be electrostatic repulsion between like charges on the polymers. Alternatively, it can be steric repulsions created by flexible solvophilic chains decorating the peptide polymers such as polyethylene glycol chains when water is the preferred solvent. These PEG segments can be attached on amino acid side-chains or on the peptide termini.

By way of illustration, we include the following example:

A large number (dozens) of systematically varied peptides (typically 7-30 residues long) have been studied in our lab for soluble polymer and gel formation in cell media. All these peptides are able to self-assemble to form beta-sheet polymers in certain low-ionic strength media, but most of them were found to precipitate out of solution in cell media. We have concluded that only peptides with a approximate net +2 or −2 charge per peptide at physiological pH=7.5, were able to form soluble polymers and gel cell media (The amount of net charge necessary per peptide to keep its polymers soluble in cell media, will vary depending on the overall surface properties and solubility of the peptide tapes it forms). Amongst the peptides we studied, peptides with +3 or −3 net charge per molecule exhibited only limited self-assembling capabilities in cell media at peptide concentration higher than 10 mg/ml and did not produce a gel matrix at any peptide concentration. Peptides with +4 or −4 net charge per molecule did not self-assemble in cell media These peptides retained a predominantly monomeric state and their solutions in cell media were fluids up to around 40 mg/ml peptide concentration.

For example, we have found that the rationally designed peptide P11-3 (SEQ ID NO: 3) in low ionic strength media at pH=7.5 does not self-assemble (peptide concentrations up to 10 mg/ml). However, when 145 mM NaCl is added in the solution or when the peptide is dissolved in cell media, it forms twisted beta-sheet fibrils, with narrow width of 4-5 nm, wide width of 12-15 nm, full pitch of 200-300 nm, and length of several micrometers (FIG. 6).

The fibrils entwine and form a three dimensional network and turn their solution in cell media into a homogeneous self-supporting gel at peptide concentration higher than 15 mg/ml (FIG. 7). The gel remains stable for at least several weeks at room temperature.

The gel can be broken by mechanical agitation. The time it takes to reform depends on the peptide concentration, ranging from seconds for a 35 mg/ml peptide gel, to hours for a 15 mg/ml peptide gel.

Similar behaviour was found for the rationally designed peptide P11-5 (Table 1; SEQ ID NO: 5) in cell media. The main difference between fibrils of P11-3 (SEQ ID NO: 3) and of P11-5 (SEQ ID NO: 5) is that those formed by P11-3 (SEQ ID NO: 3) have a net −2 negative charge per peptide at pH=7.5, whilst those formed by P11-5 (SEQ ID NO: 5) have net +2 charge per peptide at pH7.5.

Thus, it is obvious that peptide fibrils and gels with a variety of chemical properties can be produced by peptide design. For example, the type of charge (+ or −) of the polymer may be crucial for the polymer matrix-cell interactions. The nature of the neutral polar side-chains can also be varied to fine-tune and maximise the favourable polymer-cell interactions, and the polymer stability in vivo.

The fibrils and gels of P11-3 (SEQ ID NO: 3) and P11-5 (SEQ ID NO: 5) in cell media were found to reform after sterilisation using an autoclave. Thus autoclave seems to be a viable method to sterilise these peptide gels. This is very significant, since sterilisation is a prerequisite for the use of these materials with cells in vitro or in vivo. Other alternative sterilisation methods that can also be used are filtration of the initially monomeric peptide solutions or gamma irradiation. Indeed we have found that the use of gamma irradiation sterilisation is preferred since it provides a clean, straightforward and reproducible method of sterilisation. Thus, in this preferred aspect of the invention, the peptides may be dried to a powder and the dry peptide powder is subject to gamma irradiation.

Although the peptide design procedure stated above can be used to design either tapes or higher order aggregates (i.e. ribbons, fibrils and fibres) in cell media, we believe that the more robust fibrils and fibres are potentially more useful for production of peptide scaffolds for tissue engineering. The reason is that the fibrils being much stronger structural units than e.g. tapes, can support cells in three dimensions without significant breakage for a long time. In addition, the highly packed nature of the fibrils, protects the peptides from enzymatic degradation, and can increase significantly the lifetime of the scaffold in vivo.

The peptide gels are formed with a very low peptide concentration (typically above 15 mg/ml), which corresponds to 0.01 volume fraction of peptide and 0.99 volume fraction of solvent in the gel, which means that the gels contain mainly solvent. Thus, encapsulated cells in these gels, have a lot of room available to grow, to communicate with each other and nutrients, oxygen, and various metabolites can diffuse almost freely in and out of the gel network.

Injection of P11-3 (SEQ ID NO: 3) and P11-5 (SEQ ID NO: 5) peptide solutions in cell media in mice has shown no effect of the presence of the peptide in the tissue surrounding the injection site as judged by histology after two and eight weeks following the peptide injection.

The opportunities that these new biomaterials provide for tissue engineering in vitro and in vivo are enormous. A large number of different cells can be encapsulated in these polymer scaffolds.

Peptides can be designed to have a self-assembling domain followed by at least one bioactive domain. Thus, polymeric gel scaffolds can be formed in cell media, decorated with specific bioactive sequences (e.g. RGD sequence) which will control the interactions of the scaffold with a particular type of cell, and also influence the growth differentiation state and function of the encapsulated cells.

The peptide polymers (especially so the more rigid fibrils and fibres) can be preferentially aligned by shearing or application of magnetic field. Thus, anisotropic polymer scaffolds can be obtained which when they are seeded with cells, they can be particularly important for the control of cell type, cell-cell interactions and shape of the growing tissue.

The cells can be encapsulated in the polymer matrix in a variety of different ways. For example:

1) disruption of gel by mechanical agitation, mixing with the cells, and encapsulation of the cells as the gel matrix reforms around them.

2) Mix the cells with an initially fluid monomeric peptide solution in cell media, followed by triggered gel formation. The trigger can be changes of the ionic strength, small pH changes, or addition of counter ions such as Ca+2.

3) Possibly the most effective way of encapsulating cells in the peptide scaffolds is using alternating copeptides. We have indeed discovered the following:

Peptides P11-6 (SEQ ID NO: 6) and P11-7 (table 1; SEQ ID NO: 7) on their own in cell medium do not self-assemble to form long beta-sheet polymers, and for this reason their solution in cell media is fluid-like rather than gel-like. Their lack of self-assembly is attributed to their high net positive and negative charges per peptide P: −4 for P11-6 (SEQ ID NO: 6) and +4 for P11-7 (SEQ ID NO: 7). When solutions of these two peptides in cell media (peptide concentration higher than 10 mg/ml) are mixed together they spontaneously transform into a self-supporting gel, owing to the formation of heteropeptide beta-sheet polymers by these complementary interacting peptides.

Thus, it is seen that the alternating copeptide systems offer a unique way of encapsulating cells in the peptide scaffolds without the need to change the pH, ionic strength and counter ion concentration of the cell solutions. This can be done by mixing the cells with one of the initial monomeric peptide solutions, and subsequently adding the complementary peptide solution.

The heteropeptide polymers scaffolds also offer the advantage of combining different functionalities on the same polymers, and extending the chemical and periodic features of homopeptide polymers. For example one peptide component of the polymer may have a bioactive peptide bound to it, whilst its other peptide compound may have a drug molecule bound on it.

The ribbons, fibrils and/or fibres of the invention exhibit significant tensile strength, controlled, inter alia, by how many tapes make up the ribbons, fibrils or fibres, especially in the longitudinal direction of the fibril or fibre. Such strength has been estimated to be in the order of that of a conventional covalent bond. Furthermore, since the fibrils and/or fibres are biodegradable, because of their peptide content, they are especially advantageous in that they may be constructed into a biodegradable scaffold. Such scaffolds may comprise a weave, knit or plait of the fibrils or fibres of the invention.

Scaffolds can also be constructed using a combination of the peptide polymers and other commercial polymers (such as cotton and wool fibres), to obtain materials with a desirable combination of mechanical, chemical and biochemical properties, and low production cost.

Alignment of the microscopic fibrils followed by subsequent lateral association of the fibrils can result in the formation of macroscopic oriented fibre mats.

The peptide fibrils and/or fibres can be engineered to control the chemical and bioactive properties of synthetic polymer fibres. The methodology has the advantage of harnessing and combining existing expertise on manufacturing at low-cost well controlled fibrous structures with desirable mechanical properties, with the opportunity of designing their bioactivity, biocompatibility and other chemical properties. Such new materials can have exciting applications in biomedical fields such as in tissue engineering, wound healing and tissue adhesion.

Products and Applications

INDUSTRIAL APPLICATIONS

Modification of the physical and chemical properties of a surface in a controlled way, e.g. wetting properties; for example, for anti-icing applications.

Also for controlling the interaction of oil/water with clay surfaces, and the stabilising the clay itself, an important issue when, e.g. dealing with fractures in oil wells. The stability of the peptide polymers can be controlled by peptide design. Thus, by increasing the number of amino acid residues per peptide and also the number of favourable intermolecular interactions between amino acid side-chains, peptide polymers with increased stability and strength can be obtained. In addition, ribbons, fibrils and fibres can be increasingly more stable polymers compared to single tapes. Thus, the right polymers can be produced by peptide design to form gels stable in the high temperature of the oil wells. These gels can for example provide significant mechanical support at a specific site of the oil well.

Receptor or receptor binding sites can be engineered by peptide design into the ribbons, fibrils and/or fibres, providing materials for use as sensors or as biocatalysts, or as separation media in biotechnology applications.

The peptide tapes, ribbons, fibrils and fibres can be used as templates for the production of nanostructured inorganic materials with chiral pores. The dimensions, pitch and chirality of the pores can be controlled by peptide design to control the properties of the polymer aggregate. The orientation of the pores can also be controlled by alignment of the polymers in nematic states. These nanostructured materials have important applications as chiral separation media.

The fibres of the invention are advantageous because, inter alia, they possess similar properties to other known peptide fibres, for example, KEVLAR® which consists of long molecular chains produced from poly-paraphenylene terephthalamide. Thus the fibres of the invention exhibit the following features; high tensile strength at low weight, high modulus, high chemical resistance, high toughness, high cut resistance, low elongation to break, low thermal shrinkage, high dimensional stability, flame resistant and self extinguishing.

Therefore, the fibres of the invention can be processed into various forms, for example, continuous filament yarns, staple, floc, cord and fabric.

The processed fibres may possess the following characteristics: continuous filament yarn, high tensile strength, processable on conventional looms, twisters, cord forming, stranding and serving equipment; staple, very high cut resistance, spun on conventional cotton or worsted spinning equipment, precision cut short fibres, processable on felting and spun lace equipment; pulp-wet and dry, floc, precision cut short fibres, high surface area, miscible in blend composites, thermal resistance, excellent friction and wear resistance; cord, high tensile strength and modulus at low specific weight, retention of physical properties at high and low temperature extremes, very low heat shrinkage, very low creep, good fatigue resistance; fabric, excellent ballistic performance at low weights; and excellent resistance to cuts and protrusion combined with comfortable wear and excellent friction and wear performance against other materials.

The peptide fibrils and fibres of the invention may have a variety of applications, for example, in adhesives and sealants, e.g. thixotropes; in ballistics and defence, e.g. anti-mine boots, gloves—cut resistance police and military, composite helmets, and vests—bullet and fragmentation; in belts and hoses, e.g. automotive heating/cooling systems, automotive and industrial hoses, and automotive and industrial synchronous and power transmission belts; in composites, e.g. aircraft structural body parts and cabin panels, boats, and sporting goods; in fibre optic and electro-mechanical cables, e.g. communication and data transmission cables, ignition wires, and submarine, aerostat and robotic tethers; in friction products and gaskets, e.g. asbestos replacement, automotive and industrial gaskets for high pressure and high temperature environments, brake pads, and clutch linings; in protective apparel, e.g. boots, chain saw chaps, cut resistant industrial gloves, helmets—fireman and consumer (bicycle), and thermal and cut protective aprons, sleeves, etc; in tires, e.g. aircraft, automobiles, off-road, race, and trucks; and in ropes and cables, e.g. antennae guy wires, fish line, industrial and marine utility ropes, lifting slings, mooring and emergency tow lines, netting and webbing, and pull tapes.

Biomedical and Biomaterial Applications

Biocompatible surfaces: Bioresponsive and biocompatible surfaces to promote or to prevent adhesion, spreading and growth of endothelial cells in medical implant materials. Biocompatible surface coatings for devices such as stents, valves and other structures introduced into biological systems.

Tissue Engineering:

However, we have found that perhaps the most advantageous use of the peptide fibrils and/or fibres of the invention is in the construction of a biodegradable three-dimensional scaffold for use in attaching cells to produce various tissues in vivo and in vitro.

Thus according to a further feature of the invention we provide a three-dimensional scaffold comprising fibres or fibrils of the invention in cell medium. As mentioned above such scaffolds of the peptide fibrils and/or fibres are advantageous in that they can be used to support cells in the growth and/or repair of tissue. The nature of such cells may vary depending upon the nature of the tissue of interest. For example, the cells may be ligamentum cells for growing new ligaments, tenocytes for growing new tendon. Alternatively, the cells may be chondrocytes and/or other stromal cells, such as chondrocyte progenitor cells.

Therefore, according to a yet further feature of the invention we provide a three-dimensional scaffold comprising fibres or fibrils as hereinbefore described which scaffold is seeded with cells.

The methods of the invention therefore result in the efficient production of new ligament, tendon, cartilage, bone, skin, etc in vivo.

The cells may themselves be cultured in the matrix in vitro or in viva. The cells may be introduced into the implant scaffold before, during or after implantation of the scaffold. The newly grown tissue can be used to hold the scaffold in place at the site of implantation and also may provide a source of cells for attachment to the scaffold in vivo.

The ability of the polymers to break allowing the free ends to self assemble enables, for example, scaffolds to be formed in situ and also to respond (by breaking and reforming) to the growing tissue. Also monomeric peptides may be injected at the site of choice and then chemically triggered to create, for example, a gel in situ.

Thus, according to a further feature of the invention we provide a method of tissue repair which comprises seeding a three-dimensional fibre matrix as hereinbefore described with appropriate cells.

For a tendon or ligament to be constructed, successfully implanted, and function, the matrices must have sufficient surface area and exposure to nutrients such that cellular growth and differentiation can occur following implantation. The organisation of the tissue may be regulated by the microstructure of the matrix. Specific pore sizes and structures may be utilised to control the pattern and extent of fibrovascular tissue in growth from the host, as well as the organisation of the implanted cells. The surface geometry and chemistry of the scaffold matrix may be regulated to control the adhesion, organisation, and function of implanted cells or host cells.

In the preferred embodiment, the scaffold matrix is formed of peptides having a fibrous structure which has sufficient interstitial spacing to allow for free diffusion of nutrients and gases to cells attached to the matrix surface until vascularisation and engraftment of new tissue occurs. The interstitial spacing is typically in the range of 50 nm to 300 microns. As used herein, "fibrous" includes one or more fibres that is entwined with itself, multiple fibres in a woven or non-woven mesh, and sponge-like devices.

Nerve tissue engineering: The fibrils and/or fibres can be used to provide paths/tracks, to control and guide the direction of growth or movement of molecules or cells. This may be significantly useful for nerve tissue repair as well as for growth and formation of bone tissue (tissue engineering).

Bone tissue engineering: Biomineralisation using the peptide ribbons, fibrils and/or fibres as a template for the nucleation and growth of inorganic materials is important in bone tissue engineering and dental applications etc. The self assembled peptide structures have been shown to be effective as templates for hydroxyapatite crystallisation, as shown in the later examples.

Self-assembling peptides may increase mineral gain via their ability to nucleate hydroxyapatite de novo and/or by decreasing mineral dissolution via stabilisation of mineral surfaces. They are therefore candidate materials for use in both caries treatment and prevention and in treatment or prevention of bone deterioration, such as that experienced in osteoporosis.

The use of peptides, e.g. self assembling peptides (SAPs), as scaffolds in in situ tissue engineering of bone is novel per se.

Thus according to a further aspect of the invention we provide a method of tissue engineering, e.g. tissue repair, such as of bone repair, which comprises the use of a SAP as a scaffold.

Artificial skin: Network structures formed from the peptide ribbons, fibrils or fibres can be used to generate artificial skin or to promote skin regrowth in vivo.

Drug delivery: pH and ion responsive ribbons, fibrils, fibres, gels or liquid crystals are potentially useful in drug encapsulation and release and by designing an appropriate network programmable release rates may be achieved.

Personal Care Products

Dental applications: Peptide ribbons, fibrils and/or fibres are of use in the protection of teeth, as carriers for delivery of active substances to promote dental repair, as templates/scaffolds for the in situ nucleation of hydroxyapatite within tooth porosities (e.g. caries lesions, dentine), as agents for the treatment and/or prevention of caries (enamel/dentine and marginal caries around restorations), as agents for the treatment and prevention of tooth sensitivity and as carriers for the delivery of active substances into teeth. In addition, the peptide structures are of application in the treatment of dentinal/tooth staining, sensitivity and other symptoms experienced in gingival recession. The use of self assembled peptide structures in caries treatment is demonstrated in the later examples.

The prior art describes use of an amphiphilic peptide as a scaffold for ordered deposition of mineral imitating crystal orientation in bone collagen [4]. This amphiphilic peptide assembles to give a structure which forms fibrils which are stabilised by covalent modification. The assembly of this peptide differs from the self assembled peptides described here in that the assembly is driven by amphiphilic forces, rather than by very specific attractions between matched groups in the separate peptide chains. The amphiphilic peptide described is not suitable for treatment in vivo as the assembly must take place at low pH (pH<4) and the covalent modification takes place under conditions hostile to living tissues. The self assembled peptide ribbons, fibrils and fibres described in this application differ in that they can be designed such that assembly is triggered at a pH and ionic strength suitable for oral application and no subsequent reaction under hostile conditions is necessary.

The prior art also describes use of casein phosphopeptides in dental application [5]. These species are not self assembling peptides as described in this application. As shown in the examples, the self assembled peptides described in this application show improved performance in mineralisation of caries like lesions of enamel under simulated oral conditions compared with the casein phosphopeptides.

In particular, we provide a method as hereinbefore described wherein the method comprises the prevention, treatment and/or alleviation of dental caries. Thus the method may comprise the mineralisation or remineralisation of a dental cavity or the suppression of leakage around existing restorations. Alternatively, the method may comprise suppression of demineralisation.

In particular, we provide a method as hereinbefore described wherein the method comprises the prevention, treatment and/or alleviation of tooth sensitivity. Thus the method may comprise the remineralisation of a dental cavity, white spot lesions or exposed dentine. Alternatively, the method may comprise suppression of demineralisation, thus preventing development of tooth sensitivity.

Although a variety of peptides may be used, one such peptide which may be mentioned is the P11-3 peptide (SEQ ID NO: 3). A preferred group of peptides which may be mentioned are those selected from P11-1, P11-2, P11-3, P11-4, P11-5, P11-6 and P10-7 (SEQ ID NOS:-1-7, respectively).

Skin treatments: The controlled formation of peptide ribbons, fibrils and/or fibres can be of benefit in skincare and dermatological applications for both cosmetic and medical benefit. Benefits may include skin protection, improvement in skin feel, improvement of skin strength, increased suppleness, delivery of active or beneficial substances, moisturisation, improved appearance and anti-ageing effects.

Hair care products: Peptide ribbons, fibrils and/or fibres can be of benefit in hair care to improve hair condition, strength, feel, suppleness, appearance and moisturisation. Peptides which form such structures in application can be beneficial ingredients in hair shampoos, conditioners, dyes, gels, mousses and other dressings.

In another aspect of the invention responsive networks can be used to deliver perfumes, vitamins and/or other beneficial agents to the skin and/or hair. In particular, pH responsiveness can provide control of the delivery process.

The invention will now be described by way of example only and with reference to the accompanying drawings.

Example 1

Synthesis and Purification of Peptides

Peptides were synthesised using standard 9-fluorenylmethoxycarbonyl (FMOC) chemistry protocols as described in A. Aggeli et al, J. Mat. Chem., 1997. $P_{11}$-2 (SEQ ID NO: 2), $P_{11}$-3 (SEQ ID NO: 3) and $P_{11}$-5 (SEQ ID NO: 5) were purified by reversed-phase HPLC using a water-acetonitrile gradient in the presence of 0.1% trifluoroacetic acid. Mass spectrometry showed the expected molecular weights ($P_{11}$-2: m/z 1594, $P_{11}$-3: m/z 1593, $P_{11}$-5: m/z 1523). $P_{11}$-4 (SEQ ID NO: 4) was purified by reversed-phase HPLC using 0.1% ammonia in water as buffer A and 10% buffer A in acetonitrile as buffer B. Mass spectrometry showed the expected molecular weight m/z 1596.

Electron Microscopy

Samples were examined using a Phillips CM10 TEM at 80-100 kV accelerating voltage. Gels were diluted to a peptide concentration of 20 μM seconds before application to a glow-discharged, carbon-coated, copper grid followed by coating with uranyl acetate solution (4% w/v in water).

Example 2

A Rationally Designed Self-Assembling Peptide P11-3 (SEQ ID NO: 3) that Forms Solid-Like Gel Network of Interconnected Negatively Charged Fibrils in Cell Culture Medium The rationally designed peptide P11-3 (Table 1: SEQ ID NO: 3) was dissolved in 145 mM NaCi, pH~7.5 aq. solution (i.e. the ionic strength and pH values of the solution were similar to those present in cell culture medium) or it was added directly in cell culture medium. It was found that in both solutions, P11-3 (SEQ ID NO: 3) self-assembled into twisted beta-sheet fibrils, which had typically narrow width of 4-5 nm, wide width of 12-15 nm, full pitch of 200-300 nm, and length of several micrometers (FIG. 6).

The fibrils entwined partly with each other forming a three dimensional network (FIG. 4) and turned the peptide solution in cell media into a homogeneous self-supporting gel at peptide concentration higher than 15 mg/ml (FIG. 7). The gel remained stable for at least several weeks at room temperature.

The gel could be, temporarily broken by mechanical agitation. The time it took the gel to reform depended on the peptide concentration, ranging from seconds for a 35 mg/ml peptide gel, to hours for a 15 mg/ml peptide gel.

Example 3

A Rationally-Designed Self-Assembling Peptide P11-5 that Forms Solid-Like Gel Network of Interconnected Positively Charged Fibrils in Cell Culture Medium The rationally designed peptide P11-5 (Table 1) was dissolved in 145 mM NaCi, pH~7.5 aqueous solution (i.e. the ionic strength and pH values of the solution were similar to those present in cell culture medium) or it was added directly in cell culture medium. It was found that in both solutions, P11-5 self-assembled into twisted beta-sheet fibrils, which had typically narrow width of 4-5 nm, wide width of 12-15 nm, full pitch of 200-300 nm, and length of several micrometers.

The main difference between fibrils of P11-3 (example 2) and of P11-5 is that those formed by P11-3 have a net negative charge (−1 or −2) per peptide at pH=7.5, whilst those formed by P11-5 have net positive (+1 or +2) charge per peptide at pH=7.5.

The fibrils of P11-5 (SEQ ID NO: 5) entwined partly with each other forming a three dimensional network and tuned the peptide solution in cell media into a homogeneous self-supporting gel at peptide concentration higher than 15 mg/ml. The gel remained stable for at least several weeks at room temperature.

The gel could be temporarily broken by mechanical agitation. The time it took the gel to reform depended on the peptide concentration, ranging from seconds for a 35 mg/ml peptide gel, to hours for a 15 mg/ml peptide gel.

Example 4

Two Rationally-Designed Self-Assembling Peptides P11-1 (SEQ ID NO: 1) and P11-2 (SEQ ID NO: 12 that Form Insoluble Polymers that Flocculate Out of Cell Culture Medium The rationally designed peptides P11-1 and P11-2 (Table 1: SEQ ID NOS: 1 and 2, respectively) were dissolved independent of each other in 145 mM NaCl, pH~7.5 aq, solution (i.e. the ionic strength and pH values of the solution were similar to those present in cell culture medium) or added directly in cell culture medium. It was found that in both solutions, both peptides self-assembled into elongated beta-sheet polymers, but these polymers were insoluble in cell culture medium solution conditions so they rapidly flocculated out of solution, causing the solution to be a turbid fluid. Consequently these peptide polymers did not give rise to self-supporting gels in cell culture medium.

The main difference between polymers formed by either P11-3 (example 1; SEQ ID NO: 3) or P11-5 (example 2: SEQ ID NO: 5) and those formed by either P11-1 (SEQ ID NO: 1) or P11-2 (SEQ ID NO: 2) is that the former had a significant net charged whilst the latter were practically neutral in cell culture medium. The net charge carried by either P11-3 (SEQ ID NO: 3) or P11-5 (SEQ ID NO: 5) polymers caused them to repel each other and thus to remain soluble and gel the cell culture. The absence of net charge on P11-1 (SEQ ID NO: 1) or P11-2 (SEQ ID NO: 2) caused them to be insoluble and thus not to form a gel in cell culture medium conditions.

Example 5

Two Rationally-Designed Complementary Self-Assembling Peptides P11-5 (SEQ ID NO: 5) and P11-6 (SEQ ID NO: 6) that Upon Mixing, Form Solid-Like Gel in Cell Culture Medium Peptides P11-6 and P11-7 (table 1: SEQ ID NOS: 6 and 7, respectively) on their own in cell medium did not self-assemble to form long beta-sheet polymers, and for this reason their solutions in cell media remained fluid rather than gel. Their lack of self-assembly is attributed to their high (compared to P11-3 or P11-5 (SEQ ID NO: 3 and 5, respectively) net positive and negative charges per peptide: −4 for P11-6 (SEQ ID NO: 6) and +4 for P11-7 (SEQ ID NO: 7). When solutions of these two peptides in cell media (peptide concentration higher than 10 mg/ml) were mixed together, the combine solution spontaneously transformed into a self-supporting gel, owing to the formation of heteropeptide beta-sheet polymers by these complementary peptides (FIG. 3).

General Comment on the Previous Examples

All above peptides described in these examples have been rationally designed according to the molecular design principles described in this patent. Their observed behaviours have been in full agreement with the behaviours expected on the basis of the features put in the molecules by peptide design. These results demonstrate the validity of the peptide design principles claimed for the production of self-assembling peptide scaffolds, gels and nematic fluids in cell culture medium.

Example 6

The P11-3 self assembling peptide (structure given in Table 1 and SEQ ID NO: 3) was assembled into its gel form by mixing with a solution supersaturated with respect to hydroxyapatite at pH 7.4. The P11-3 (SEQ ID NO: 3) gel was incubated for 7d at 37° C. The gel was then washed and prepared for TEM, EDX and electron diffraction analyses. TEM showed deposits of electron dense, crystal-like material. Electron diffraction and EDX showed that the electron-dense material was apathetic (Ca:P=1.66).

This example demonstrates that SAP gels can nucleate the formation of hydroxyapatite crystals de novo and hence could be used in bone engineering applications and bone treatments.

Example 7

Gelatin was mixed with a solution supersaturated with respect to hydroxyapatite at pH 7.4. The resultant gel had similar viscosity and organic concentration to the P11-3 (SEQ ID NO: 3) gel described in the previous example. The gelatin gel was incubated for 7d at 37° C. The gel was then washed and prepared for TEM, EDX and electron diffraction analyses. TEM showed no crystalline deposits in the gel.

This example demonstrates that proteinaceous gels of similar constitution to the SAP gels do not nucleate the formation of hydroxyapatite crystals in the same way that the SAP gels do.

Example 8

Caries-like lesions were created in areas of sound enamel of human whole extracted permanent teeth by immersion in acidified gelatin gels for 6 weeks. Monomeric SAP (P11-3) solution (10 μL of a 1% peptide solution, pH 8) was applied directly to the surfaces of the lesions which were then cycled for 5 d with 3×20 min. acid challenges per day in the Leeds oscillating pH model (Robinson et al. Caries Res. 26: 14-17 (1992)) to simulate intra-oral conditions. Control lesions were cycled without SAP application. Further controls used poly-GLU peptides (Mr=750 D) in place of SAP. Mineral loss or gain was calculated by determination of P in the supernatant solutions. The surfaces of the cycled teeth were also examined by SEM.

Results showed that net mineral gain by the lesions after cycling was significantly increased following a single SAP application (35±2 μg P/mm$^2$ enamel compared with 5±4 μg P/mm$^2$ for controls, n=7, p<0.001). This was apparently due to significantly decreased demineralisation (8±5 μg P/mm$^2$ compared with 20±10 μg P/mm$^2$ for controls, p<0.01) and increased remineralisation (43±5 μg P/mm$^2$ compared with 25±10 μg P/mm$^2$ for controls, p=0.06). Increase in net mineral gain by the lesions after SAP application was evident on each of the 5 days of cycling. SEM of the SAP treated cycled tooth surfaces showed no indication of surface deposits suggesting mineral deposition had occurred within the body of the lesion. Lesions treated with poly-GLU behaved similarly to untreated controls, indicating a specific effect for SAP in this system.

The example demonstrates that self assembling peptides designed to form ribbons, fibrils and fibres under oral conditions are effective in promoting remineralisation of dental tissue in contrast to other peptides such as poly-GLU which are not effective.

Example 9

Caries-like lesions were created in areas of sound enamel of human whole extracted permanent teeth by immersion in acidified gelatin gels for 6 weeks. The lesions were then cycled for 5 d with 3×20 min. acid challenges per day interspersed with 2×10 minute immersion in a solution of casein phosphopeptide in the Leeds oscillating pH model (Robinson et al. Caries Res. 26: 14-17 (1992)) to simulate intra-oral conditions. Control lesions were cycled without casein phosphopeptide application. Mineral loss or gain was calculated by determination of P in the supernatant solutions.

Results showed that net mineral gain by the lesions after cycling was not significantly different with repeated treatment by casein phosphopeptide versus the control.

The example demonstrates that other peptides such as casein phosphopeptide which have been claimed to be effective in dental remineralisation are not as effective as self assembling peptides designed to form ribbons, fibrils and fibres under oral conditions. Even with the greater degree of exposure provided by repeated immersion in casein phosphopeptide solution, this treatment was not as effective as one application of a self assembled peptide designed for the purpose, as exemplified above.

Example 10

Biocompatibility of Peptide Gels

Two peptide gels of potential as scaffolds in tissue engineering applications were investigated for their biocompatibility in vitro. The peptides were gamma irradiated in their dry form and then allowed to form gels in DMEM (20 mg/ml). The peptide gels were placed on a lawn of freshly seeded L929 fibroblasts and cultures incubated under standard conditions for 2 days. The culture medium was then removed and the cells stained with crystal violet. Images were captured digitally.

Fibroblasts grew up to and on gels formed from DN1-2E and DN1-2O (FIG. 8, FIG. 9) demonstrating the biocompatibility of the peptide gel scaffolds.

Table Legends

Table 1 (SEQ ID NOS: 1-7):

Primary structures of the rationally designed peptides used as example in the description. The one-letter amino-acid code is used. The N- and C-termini of the peptides are always blocked with $CH_3CO-$ and $NH_2-$ respectively. O symbolises ornithine amino acid side chains.

Schematic representation of peptides in beta-strand conformation (represented as vertical lines) hydrogen bonding in one dimension with each other to form long self-assembling beta-sheet tapes. The width of the tape is determined by the length of the peptide molecules. The thickness of the tape is equal to the thickness of a beta-strand. The surface properties of the tapes are defined by the end groups of the peptide amino acid side-chains. The tapes are also shown to entangle to form a gel network in a good solvent.

Figure 1:
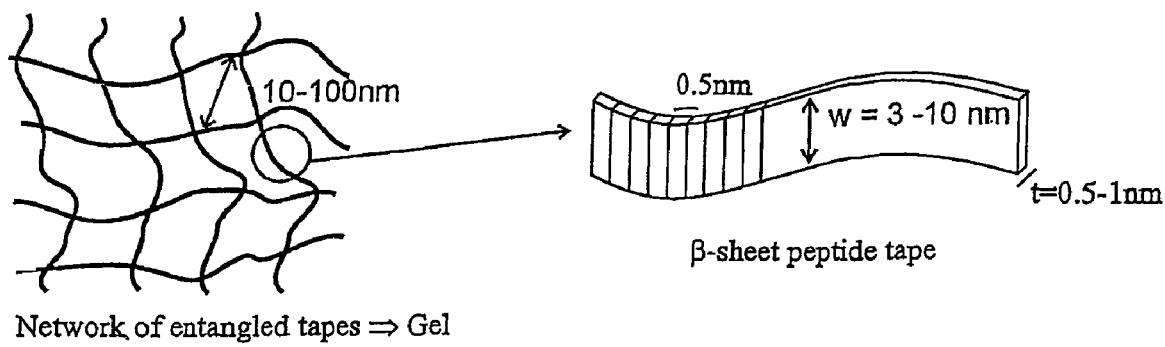
FIG. 1.
Figure 2:
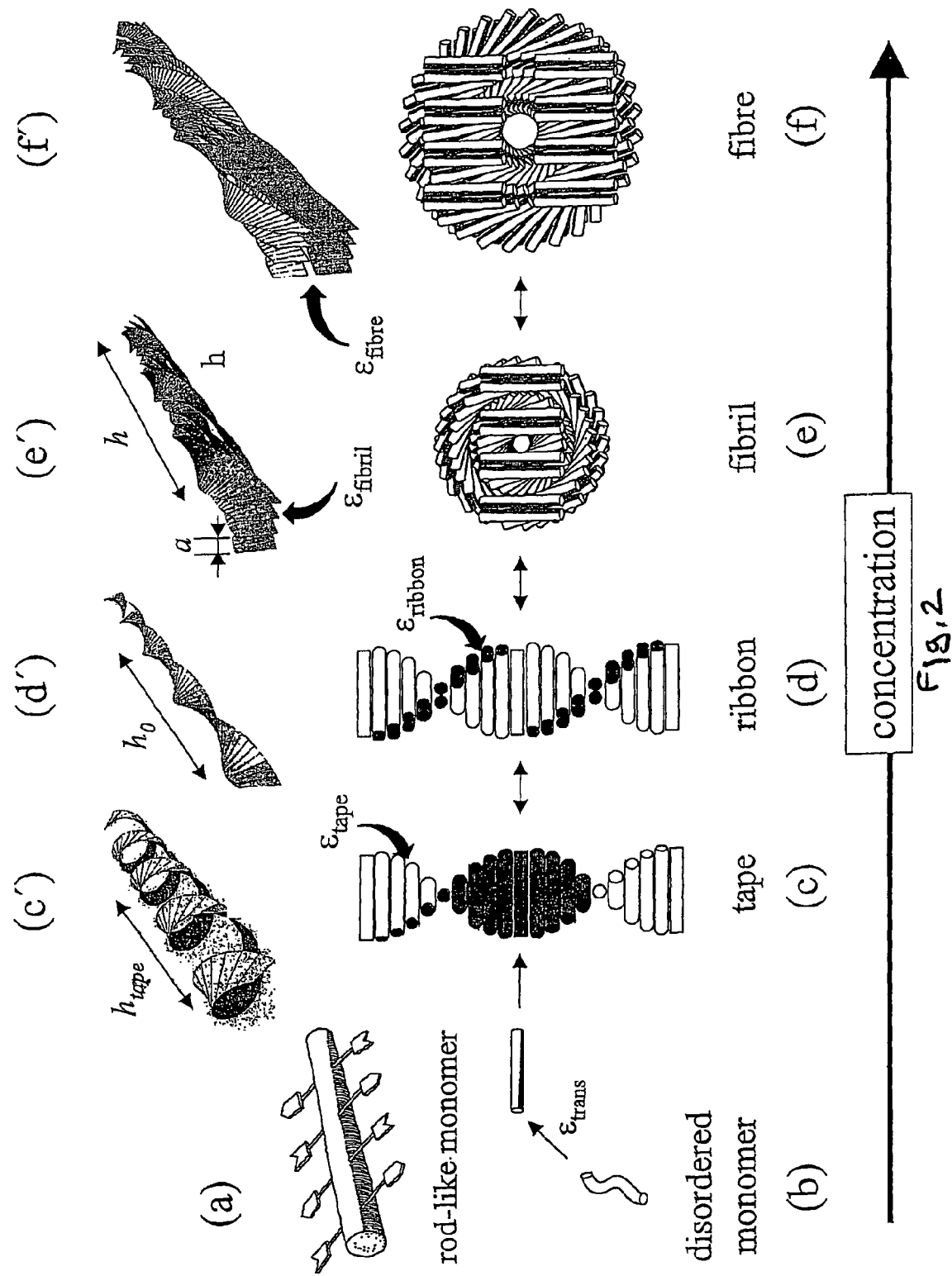
Figure 3:
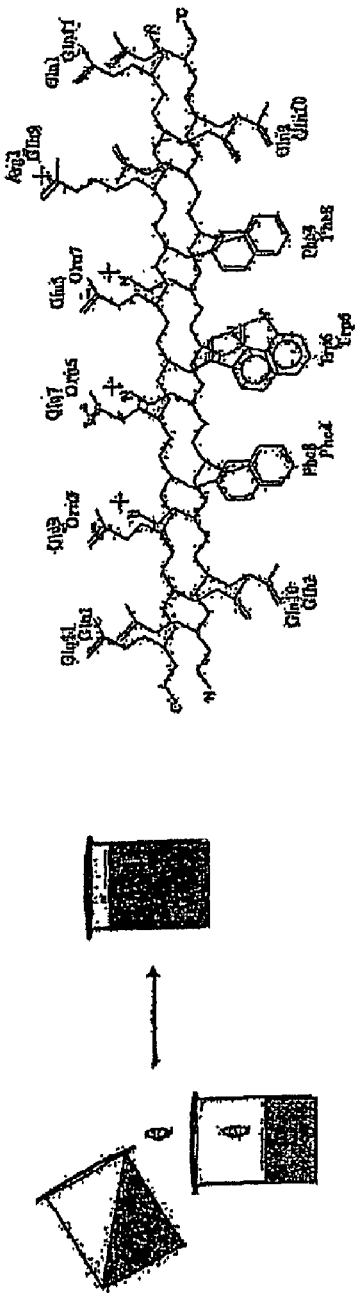
Figure 4:
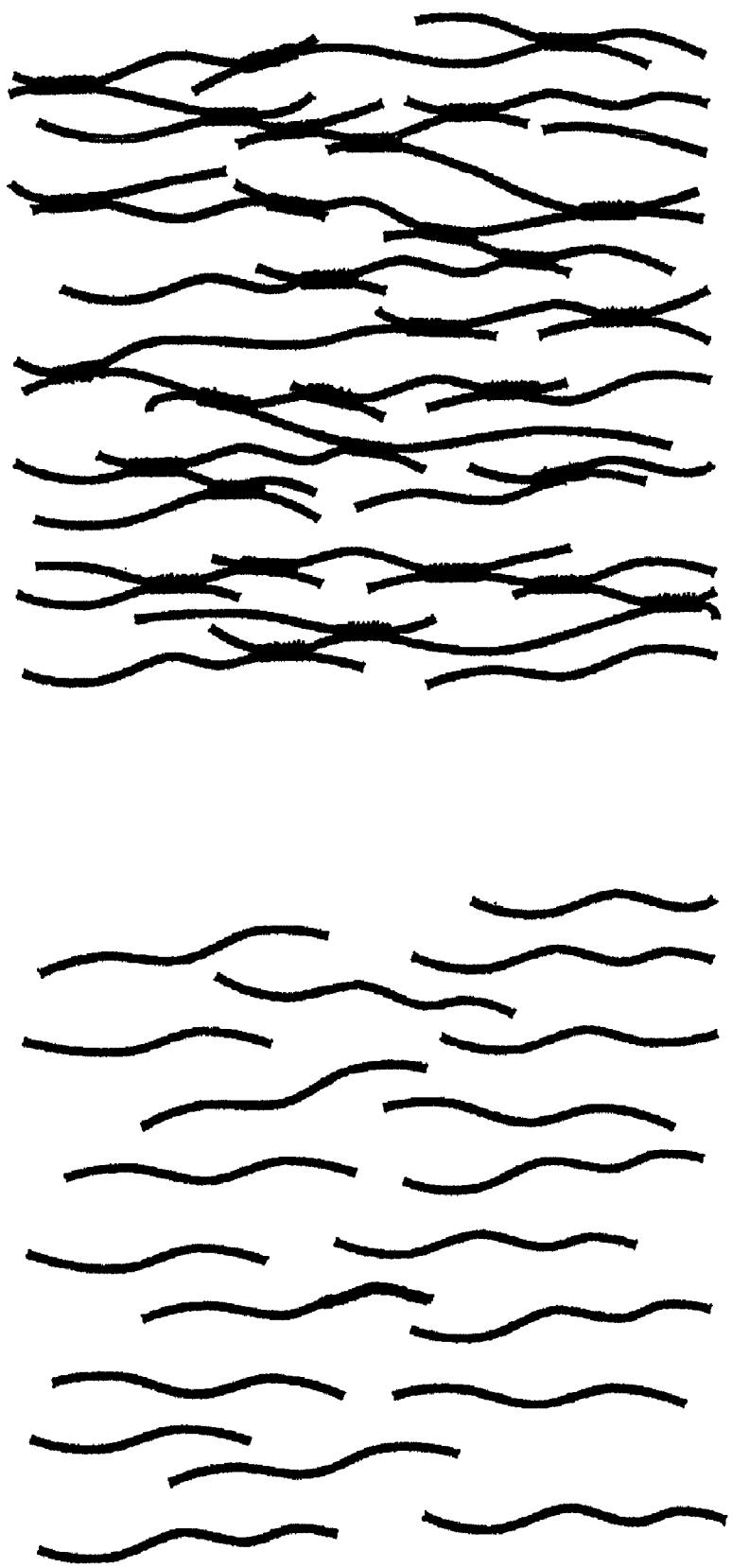
Figure 6:
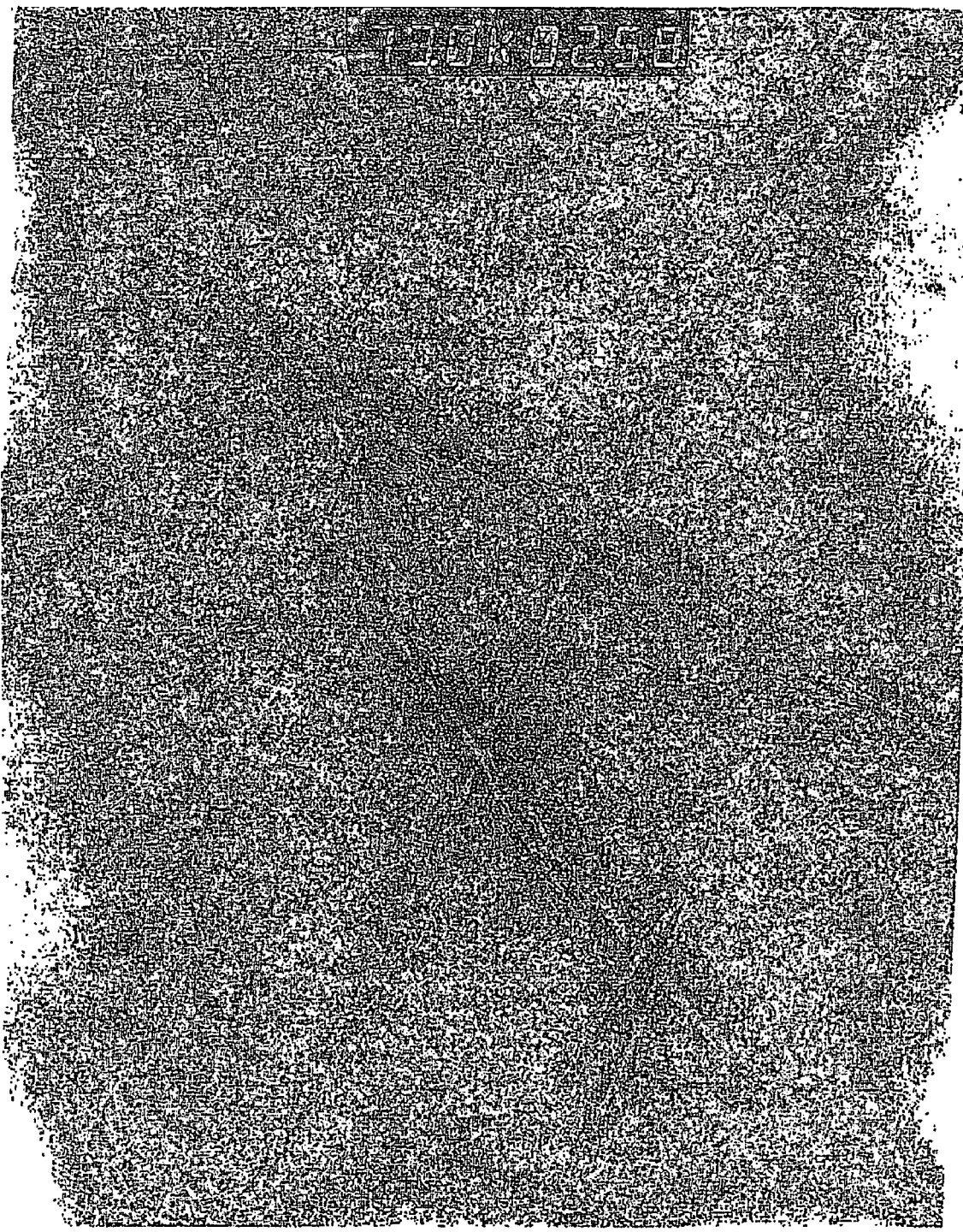
Figure 7:
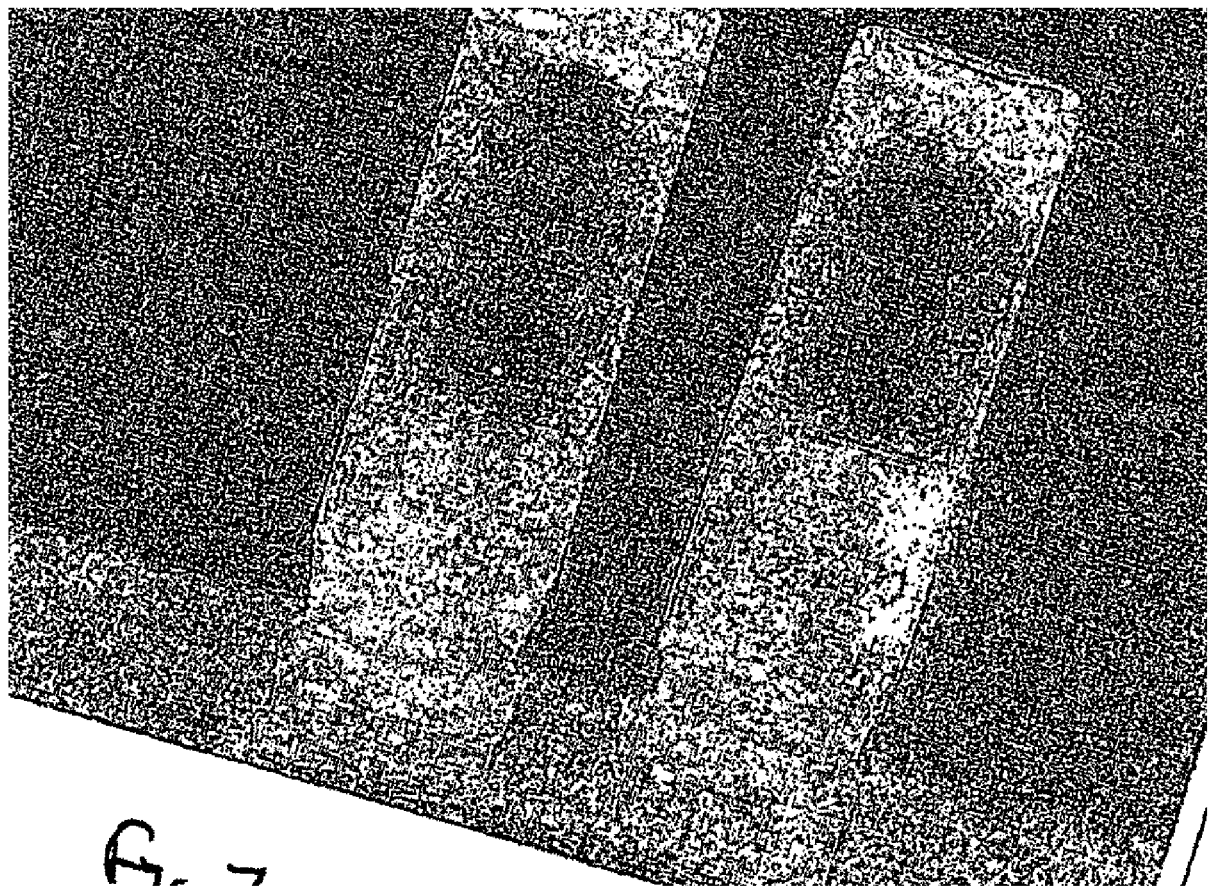
Figure 8:
Figure 9:
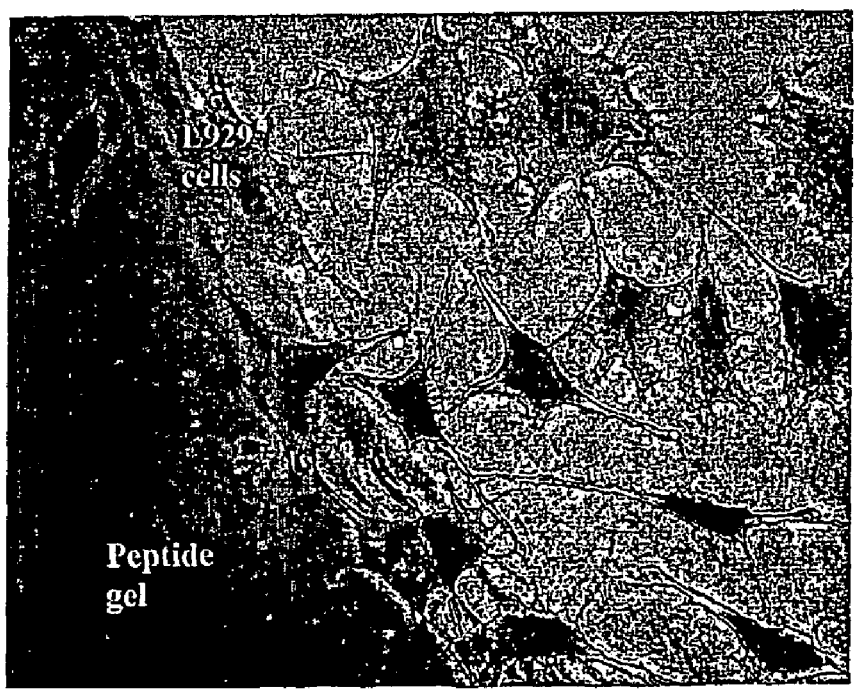

FIG. 2. Model of hierarchical self-assembly of beta-sheet forming peptides. Each peptide in beta-strand conformation, is depicted as a chiral rod-like unit (a). Local arrangements (c-f) and the corresponding global equilibrium conformations (c'-f') for the hierarchical self-assembling structures formed in solutions of chiral molecules (a), which have complementary donor and acceptor groups, shown by arrows, via which they interact and align to form tapes (c). The black and the white surfaces of the rod (a) are reflected in the sides of the helical tape (c) which is chosen to curl towards the black side (c'). The outer sides of the twisted ribbon (d), of the fibril (e) and of the fibre (f) are all white. One of the fibrils in the fibre (f') is drawn with darker shade for clarity. (e) & (f) show the front views of the edges of fibrils and fibres, respectively. Geometrical sizes (the numbers in parentheses show the values of the corresponding geometric sizes for $P_{11}$-I and $P_{11}$-II peptides, based on X-ray diffraction data and molecular modelling): inter-rod separation in a beta-sheet tape $b_2$ ($b_2=0.47$ nm); tape width, equal to the length of a rod, $b_1$ ($b_1=4$ nm); inter-ribbon distance in the fibril, $\alpha$ ($\alpha=1.6-2$ nm for $P_{11}$-I, and $\alpha=2-2.4$ nm for $P_{11}$-II).

FIG. 3:

Alternating copeptide polymeric gels.

FIG. 4:

Schematic representation of orientation of the semi-rigid fibrils in solution to form nematic liquid crystalline solutions. At higher peptide concentration, the fibrils entwine frequently with each other to form fibre-like junctions and cause formation of an anisotropic three-dimensional matrix and gelation of the liquid crystalline solution.

FIG. 5:

List of components of typical cell medium

FIG. 6:

Transmission electron micrograph of fibrils making up the P11-3 peptide gel network in cell media. Total magnification: X 180, 000.

FIG. 7:

Photographs of inversed self-supporting peptide gels (35 mg/ml P11-3) in 145 mM NaCl in water (left) and in cell medium (right).

FIG. 8:

Fibroblasts growing up to and on gels formed demonstrating the biocompatibility of the peptide gel scaffolds of DN1-2E (×400).

FIG. 9:

Fibroblasts growing up to and on gels formed demonstrating the biocompatibility of the peptide gel scaffolds of DN1-2O (×400).

REFERENCES

1. Aggeli, A., Boden, N., Semenov, A. et al, Exploiting protein folding and misfolding to engineer nanostructured materials, *The Biochemist,* 22, 10-14, 2000.
2. Nyrkova, I A, Semenov, A N, Aggeli, A & Boden, N, Fibril stability in solutions of twisted beta-sheet peptides: a new kind of micellisation in chiral systems, *Eur Phys J B,* 17, 481-497, 2000.
3. Nyrkova, I A, Semenov, A N, Aggeli, A, Bell, M., Boden, N & McLeish, T C B, Self-assembly and structure transformations in living polymers forming fibrils, *Eur Phys J B,* 17, 499-513, 2000.
4. Hartgerink J D, Beniash E, Stupp S I Self assembly and mineralisation of peptide-amphiphile nanofibers SCIENCE 294 (5547): 1684-1688 Nov. 23 2001.
5. Advances in enamel remineralisation: Casein phosphopeptide-amorphous calcium Phosphate Reynolds E C, Black C L, Cai F, Cross K J, Eakins D, Huq N L, Morgan M V, Nowicki A, Perich J W, Riley P F, Shen P, Talbo G, Webber F JOURNAL OF CLINICAL DENTISTRY 10 (2): 86-88 1999

The invention claimed is:

1. A composition comprising:
ribbons, fibrils or fibres, wherein each of the ribbons, fibrils or fibres has an antiparallel arrangement of peptides in a β-sheet tape-like substructure at physiological pH, wherein each peptide comprises a net −2 or +2 charge, and wherein the peptide is P11-3; and sodium chloride concentration equal to or about 145 mM,
wherein the composition is at a physiological pH, and wherein the peptide is present at a concentration of greater than 15 mg/ml in the composition.

2. The composition of claim 1, wherein the composition comprises a self assembling peptide (SAP) or complementary SAPs, wherein the SAP forms a tape in an aqueous medium and is made up of 3 or more polar/neutral amino acids and a plurality of charged amino acids.

3. The composition according to claim 2, wherein the ratio of total amino acids to net charged amino acids is from 11:1 to 11:3.

4. The composition according to claim 2, wherein the polar/neutral amino acids comprise glutamine, serine, asparagine, glutamic acid, ornithine, cysteine, lycine, histidine or threonine.

5. The composition according to claim 2, wherein the amino acids are positively charged and form a gel at a pH of less than or equal to a neutral pH.

6. The composition according to claim 2, wherein the amino acids are negatively charged and form a gel at a pH of greater than or equal to a neutral pH.

7. The composition according to claim 2, wherein the amino acid chain is extended to include a bioactive peptide sequence.

8. The composition according to claim 2, wherein the amino acid chain is attached to a therapeutically active molecule.

9. The composition according to claim 1, wherein the composition comprises a SAP which forms ribbons and/or fibrils in an aqueous solution and wherein the SAP has a primary structure in which at least 50% of the amino acids comprise an alternating structure of polar and apolar amino acids.

10. The composition according to claim 9, wherein the polar amino acids include from 1 to 3 net charged amino acids per 11 amino acids.

11. The composition according to claim 9, wherein the composition comprises a self assembling peptide (SAP) wherein the SAP forms a tape in an aqueous medium and is made up of 3 or more polar/neutral amino acids and a plurality of charged amino acids.

12. The composition according to claim 9, wherein the apolar amino acids comprise phenylalanine, tryptophan, valine, leucine, isoleucine or methionine.

13. The composition according to claim 11, wherein the amino acid chain is extended to include a bioactive peptide sequence.

14. The composition according to claim 11, wherein the amino acid chain is attached to a therapeutically active molecule.

15. The composition according to claim 9, wherein the SAP is soluble in a highly ionic medium.

16. The composition according to claim 15, wherein the SAP comprises a ratio of net charged amino acids to total amino acids of from 1:11 to 4:11.

17. The composition according to claim 1, wherein the persistence length of the ribbons, fibrils or fibres is from 20 nm-70 µm.

18. The composition according to claim 17, wherein the peptide is a P11-3 variant.

19. The composition according to claim 1, wherein the composition substantially comprises ribbons, fibrils, or fibres.

20. The composition according to claim 19, wherein the composition substantially comprises fibrils, and wherein the fibrils are comprised in a network of fibrils interconnected at fibre-like junctions.

21. The composition according to claim 1, wherein a solution of the composition has a nematic transition occurring at $C_{I/N}$=0.9 mM.

22. The composition according to claim 19, wherein the fibrils or fibres are in the form of a nematic fluid.

23. The composition according to claim 22, wherein the nematic fluid is an elastomeric gel.

24. The composition according to claim 1, wherein the material is in the form of a tissue engineering scaffold.

25. The composition according to claim 24, wherein the scaffold is seeded with cells.

26. The composition according to claim 25, wherein the cells are ligamentum cells for growing new ligaments, tenocytes for growing new tendon, chondrocytes for cartilage, osteoblasts for bone, cardiac cells for cardiac tissue engineering, stromal cells for tissue patches, fibroblasts and keratinocytes for skin and mesenchymal stem cells for any of these applications.

27. The composition according to claim 1, wherein the composition possess one or more of high tensile strength at low weight, high modulus, high chemical resistance, high toughness, high cut resistance, low elongation to break, low thermal shrinkage, high dimensional stability, flame resistant, or self extinguishing.

28. The composition according to claim 1, wherein the fibres possess characteristics selected from the following: continuous filament yarn, high tensile strength, processable on conventional looms, twisters, cord forming, stranding and serving equipment; staple, very high cut resistance, spun on conventional cotton or worsted spinning equipment, precision cut short fibres, processable on felting and spun lace equipment; pulp-wet and dry, floc, precision cut short fibres, high surface area, miscible in blend composites, thermal resistance, excellent friction and wear resistance; cord, high tensile strength and modulus at low specific weight, retention of physical properties at high and low temperature extremes, very low heat shrinkage, very low creep, good fatigue resistance; fabric, excellent ballistic performance at low weights; and excellent resistance to cuts and protrusion combined with comfortable wear and excellent friction and wear performance against other materials.

29. The composition according to claim 1, wherein the material comprises a skin treatment.

30. The composition according to claim 29, wherein the skin treatment comprises skincare and dermatological applications for cosmetic and/or medical treatment.

31. The composition according to claim 29, wherein the skin treatment comprises one or more of skin protection, improvement in skin feel, improvement of skin strength, increased suppleness, delivery of active or beneficial substances, moisturisation, improved appearance and/or anti-ageing effects.

32. The composition according to claim 1, wherein the composition comprises a hair care product.

33. The composition according to claim 32, wherein the hair care product improves hair condition, strength, feel, suppleness, appearance and/or moisturisation.

34. The composition according to claim 33, wherein the hair care product comprises a hair shampoo, conditioner, dye, gel, mousse and/or other dressing.

35. The composition according to claim 1, wherein the material comprises a network adapted for the delivery of perfumes, vitamins and/or other beneficial agents to the skin and/or hair.

36. The composition according to claim 35, wherein pH responsiveness is used to control delivery.

37. The composition according to claim 1, wherein the material is sterilised.

38. A method of tissue engineering, comprising seeding the composition of claim 1 with cells.

39. A method for bone repair comprising applying the composition of claim 1 as a scaffold.

40. A method of sterilising the composition according to claim 1, comprising gamma irradiation of a dry powder of the composition.

41. The composition according to claim 1, wherein the composition can modify wetting properties or anti-icing properties of a material, control interaction of oil/water with clay surfaces, stabilize clay, or deal with fractures in oil-wells.

42. The composition according to claim 1, wherein the composition is part of a sensor, biocatalyst or separation media in biotechnology applications.

43. The composition according to claim 1, wherein the composition is part of a bioresponsive and biocompatible surface.

44. The composition according to claim 1, wherein the composition can serve as a template for nucleation and growth of inorganic materials.

45. The composition according to claim 1, wherein the composition comprises continuous filament yarns, staple, floc, cord, or fabric.

46. The composition according to claim 1, further comprising a polymer.

47. A composition comprising:
ribbons, fibrils or fibres, wherein each of the ribbons, fibrils or fibres has an antiparallel arrangement of peptides in a β-sheet tape-like substructure at physiological pH, wherein each peptide comprises a net −2 or +2 charge, and wherein the peptide is P11-3; and a sodium chloride concentration equal to or about 145 mM, wherein the composition is at a physiological pH, and wherein the peptide is at a concentration of 15 mg/ml to 35 mg/ml in the composition.

48. The composition of claim 1, wherein the pH is about 7.5.

* * * * *